US012605306B2

(12) United States Patent
Kakinuma

(10) Patent No.: US 12,605,306 B2
(45) Date of Patent: Apr. 21, 2026

(54) METHOD OF MANUFACTURING MONOMER COMPOSITION, RAW MATERIAL COMPOSITION, MONOMER COMPOSITION, CURABLE COMPOSITION, AND MOLDED BODY

(71) Applicant: MITSUI CHEMICALS, INC., Tokyo (JP)

(72) Inventor: Naoyuki Kakinuma, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 599 days.

(21) Appl. No.: 17/628,600

(22) PCT Filed: Aug. 7, 2020

(86) PCT No.: PCT/JP2020/030437
§ 371 (c)(1),
(2) Date: Jan. 20, 2022

(87) PCT Pub. No.: WO2021/033585
PCT Pub. Date: Feb. 25, 2021

(65) Prior Publication Data

US 2022/0249331 A1 Aug. 11, 2022

(30) Foreign Application Priority Data

Aug. 20, 2019 (JP) ................................ 2019-150510

(51) Int. Cl.
*A61K 6/62* (2020.01)
*A61K 6/889* (2020.01)
*C08F 290/06* (2006.01)
*C08G 18/22* (2006.01)
*C08G 18/81* (2006.01)

(52) U.S. Cl.
CPC ................ *A61K 6/62* (2020.01); *A61K 6/889* (2020.01); *C08F 290/06* (2013.01); *C08G 18/22* (2013.01); *C08G 18/81* (2013.01)

(58) Field of Classification Search
CPC ...................................................... A61K 6/887
See application file for complete search history.

(56) References Cited

U.S. PATENT DOCUMENTS

| | | | | |
|---|---|---|---|---|
| 3,825,518 | A | | 7/1974 | Foster et al. |
| 3,862,920 | A | | 1/1975 | Foster et al. |
| 4,437,960 | A | * | 3/1984 | Zengel ............... C08G 59/4035 204/500 |
| 2010/0204434 | A1 | | 8/2010 | Ludewig et al. |
| 2011/0112269 | A1 | | 5/2011 | Iwazumi et al. |

FOREIGN PATENT DOCUMENTS

| | | | | |
|---|---|---|---|---|
| CA | 2792217 | A1 | | 4/2013 |
| EP | 3 871 650 | A1 | | 9/2021 |
| JP | S51-036960 | A | | 3/1976 |
| JP | S51-036960 | B2 | | 10/1976 |
| JP | H03-146513 | A | | 6/1991 |
| JP | 2002121379 | A | * | 4/2002 |
| JP | 2007-326971 | A | | 12/2007 |
| JP | 2010-185074 | A | | 8/2010 |
| JP | 2010215774 | A | * | 9/2010 |
| JP | 2012-102086 | A | | 5/2012 |
| JP | 2013-087287 | A | | 5/2013 |
| JP | 2016219497 | A | * | 12/2016 |
| JP | 2018-203946 | A | | 12/2018 |
| JP | 2018-203947 | A | | 12/2018 |
| WO | 2010/001550 | A1 | | 1/2010 |
| WO | 2013/099766 | A1 | | 7/2013 |

OTHER PUBLICATIONS

English machine translation of Kojima et al. (JP 2010-215774). (Year: 2010).*
English machine translation of Iryo et al. (JP 2002-121379) (Year: 2002).*
Urakawa (JP 2016-219497) English machine translation (Year: 2016).*

* cited by examiner

*Primary Examiner* — Michael F Pepitone
(74) *Attorney, Agent, or Firm* — BUCHANAN INGERSOLL & ROONEY PC

(57) ABSTRACT

A method of manufacturing a monomer composition includes a step of mixing a zinc catalyst (A), an iso(thio)cyanate compound (B) having an iso(thio)cyanate group, and an alcohol compound (C) having a hydroxy group, and at least one of the iso(thio)cyanate compound (B) or the alcohol compound (C) has a (meth)acryloyl group.

15 Claims, No Drawings

METHOD OF MANUFACTURING MONOMER COMPOSITION, RAW MATERIAL COMPOSITION, MONOMER COMPOSITION, CURABLE COMPOSITION, AND MOLDED BODY

CROSS-REFERENCE OF RELATED APPLICATIONS

This application is a U.S. National Stage Application of PCT/JP2020/030437, filed Aug. 7, 2020, which claims priority to Japanese Patent Application No. 2019-150510, filed Aug. 20, 2019, the entire contents of all of which are hereby incorporated by reference.

TECHNICAL FIELD

The present invention relates to a method of manufacturing a monomer composition, a raw material composition, a monomer composition, a curable composition, and a molded body.

BACKGROUND ART

As an example of a monomer contained in a curable composition, urethane (meth)acrylate that is a (meth)acrylate compound having an urethane bond is known.

Conventionally, urethane (meth)acrylate has been synthesized using a Sn (tin) catalyst.

For example, Patent Literature 1 discloses a dental composite filler that is a mixture of fine inactive inorganic filler powders and a reaction product of an organic diisocyanate and an oxyalkyl acrylate or an oxyalkyl methacrylate. In the example of Patent Literature 1, dibutyltin dilaurate is used as a catalyst, and oxypropyl methacrylate is reacted with 2,2,4-trimethylhexamethylene diisocyanate to form diurethane dimethacrylate.

[Patent Literature 1] Japanese Examined Patent Publication (JP-B) No. S51-36960

SUMMARY OF INVENTION

Technical Problem

Recently, from the viewpoint of a reduction in heavy metal usage, as a catalyst for forming urethane (meth) acrylate, a catalyst that replaces a Sn catalyst (for example, dibutyltin dilaurate (DBTDL)) has been required.

In a case in which an iso(thio)cyanate compound having an iso(thio)cyanate group is reacted with a (meth)acrylate compound having a hydroxy group using a catalyst to form urethane (meth)acrylate, it is desired that the obtained urethane(meth)acrylate has high purity. Further, in a case in which a cured product is formed by using a composition containing the obtained urethane (meth)acrylate, it is desired that the cured product is excellent in mechanical properties such as an elastic modulus, breaking strength, breaking energy and the like.

A problem of one aspect of the present disclosure is to provide a method of manufacturing a monomer composition in which urethane (meth)acrylate can be manufactured by using a catalyst that replaces a Sn catalyst and a cured product excellent in mechanical properties can be manufactured, a raw material composition in which urethane (meth) acrylate can be manufactured by using a catalyst that replaces a Sn catalyst and a cured product excellent in mechanical properties can be manufactured, a monomer composition in which a cured product excellent in mechanical properties can be manufactured, a curable composition containing the above described monomer composition, and a molded body that is a cured product of the above described composition.

Solution to Problem

The means for solving the above described problem are as follows.

<1> A method of manufacturing a monomer composition, comprising a step of mixing a zinc catalyst (A), an iso(thio)cyanate compound (B) having an iso(thio) cyanate group, and an alcohol compound (C) having a hydroxy group, wherein at least one of the iso(thio)cyanate compound (B) or the alcohol compound (C) has a (meth)acryloyl group.

<2> The method of manufacturing a monomer composition according to <1>, wherein the zinc catalyst (A) is at least one of a sulfur-containing compound containing a sulfur atom or an oxygen-containing compound containing an oxygen atom.

<3> The method of manufacturing a monomer composition according to <1> or <2>, wherein the zinc catalyst (A) is at least one of a compound represented by the following formula (1) or a compound represented by the following formula (2).

(1)

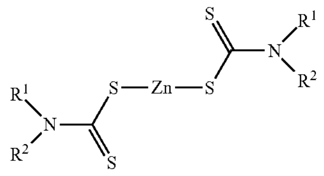

(2)

$$R^3—X^1—Zn—X^2—R^4$$

In formula (1), $R^1$ and $R^2$ are each independently a monovalent hydrocarbon group, and two $R^1$ and two $R^2$ may be the same or different, respectively. In formula (2), $X^1$ and $X^2$ are each independently an oxygen atom or a sulfur atom. $R^3$ and $R^4$ are each independently a monovalent organic group having an aromatic ring or a heterocycle, or $R^3$ and $R^4$ are organic groups that combine with each other to form a ring structure.

<4> The method of manufacturing a monomer composition according to any one of <1> to <3>, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth)acrylate.

<5> The method of manufacturing a monomer composition according to any one of <1> to <4>, wherein the alcohol compound (C) is at least one selected from the group consisting of 2-hydroxyethyl(meth)acrylate, 2-hydroxypropyl(meth)acrylate, 2-hydroxybutyl(meth) acrylate, 2-hydroxy-3-phenoxypropyl(meth)acrylate, 4-hydroxybutyl(meth)acrylate, 1,4-cyclohexanedimethanol mono(meth)acrylate, ethylene glycol and glycerin.

<6> A raw material composition, comprising: a zinc catalyst (A), an iso(thio)cyanate compound (B) having an iso(thio)cyanate group, and an alcohol compound (C) having a hydroxy group, wherein at least one of the iso(thio)cyanate compound (B) or the alcohol compound (C) has a (meth)acryloyl group.

<7> A monomer composition containing a zinc catalyst (A) and a (meth)acrylate compound (D) that is a reaction product of an iso(thio)cyanate compound (B) having an iso(thio)cyanate group, and an alcohol compound (C) having a hydroxy group.

<8> The monomer composition according to <7>, wherein the zinc catalyst (A) is at least one of a compound represented by the following formula (1) or a compound represented by the following formula (2).

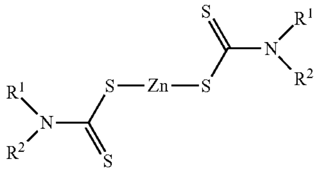

(1)

$$R^3—X^1—Zn—X^2—R^4$$ (2)

In formula (1), le and $R^2$ are each independently a monovalent hydrocarbon group, and two $R^1$ and two $R^2$ may be the same or different, respectively. In formula (2), $X^1$ and $X^2$ are each independently an oxygen atom or a sulfur atom. $R^3$ and $R^4$ are each independently a monovalent organic group having an aromatic ring or a heterocycle, or $R^3$ and $R^4$ are organic groups that combine with each other to form a ring structure.

<9> The monomer composition according to <7> or <8>, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis (isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth) acrylate.

<10> The monomer composition according to any one of <7> to <9>, wherein the alcohol compound (C) is at least one selected from the group consisting of 2-hydroxyethyl(meth)acrylate, 2-hydroxypropyl(meth) acrylate, 2-hydroxybutyl(meth)acrylate, 2-hydroxy-3-phenoxypropyl(meth)acrylate, 4-hydroxybutyl(meth) acrylate, 1,4-cyclohexanedimethanol mono(meth) acrylate, ethylene glycol and glycerin.

<11> A curable composition containing the monomer composition according to any one of <7> to <10>.

<12> The curable composition according to <11>, further comprising a polymerization initiator.

<13> A composition for a dental material comprising the curable composition according to <11> or <12>.

<14> A molded body that is a cured product of the curable composition according to any one of <11> to <13>.

Effects of Invention

According to one aspect of the present disclosure, a method of manufacturing a monomer composition in which urethane (meth)acrylate can be manufactured by using a catalyst that replaces a Sn catalyst and a cured product excellent in mechanical properties can be manufactured, a raw material composition in which urethane (meth)acrylate can be manufactured by using a catalyst that replaces a Sn catalyst and a cured product excellent in mechanical properties can be manufactured, a monomer composition in which a cured product excellent in mechanical properties can be manufactured, a curable composition containing the above described monomer composition, and a molded body that is a cured product of the above described composition, are provided.

DESCRIPTION OF EMBODIMENTS

Mode for Carrying Out the Invention

In the present disclosure, the numerical range represented by "A to B" includes A and B as a minimum value and a maximum value, respectively.

In the present disclosure, the "process" refers not only to a process that is independent from the other steps, but also to a step that cannot be clearly distinguished from the other steps, as long as the aim of the process is achieved.

In the present disclosure, in a case in which there are more than one kind of substances corresponding to a component of a composition, the amount of each component in the composition refers to the total amount of the plural substances existing in the composition, unless otherwise stated.

In the present disclosure, when numerical ranges are described in a stepwise manner, the upper limit value or the lower limit value of a numerical range may be replaced with the upper limit value or the lower limit value of other numerical range. In a numerical range described in the present disclosure, the upper limit or the lower limit of the numerical range may be replaced with a relevant value indicated in any of Examples.

In the present disclosure, "(meth)acryloyl" means acryloyl or methacryloyl, and "(meth)acrylate" means acrylate or methacrylate.

In the present disclosure, "iso(thio)cyanate" means isocyanate or isothiocyanate.

In the present disclosure, —NHC(═O)O— bond and —NHC(═S)O— bond are collectively referred to as "urethane bond", and a compound that has at least one of —NHC(═O)O— bond and —NHC(═S)O— bond, and has a (meth)acryloyl group is also referred to as urethane (meth) acrylate.

The preferred configurations described in the method of manufacturing a monomer composition, the raw material composition, the monomer composition, the curable composition, and the molded body in the present disclosure may be appropriately combined. For example, the configurations described in the raw material composition may be appropriately combined with the monomer composition, the method of manufacturing a monomer composition, and the like.

[Raw Material Composition]

The raw material composition in the present disclosure contains a zinc catalyst (A), an iso(thio)cyanate compound (B) having an iso(thio)cyanate group (also referred to as "iso(thio)cyanate compound (B)"), and an alcohol compound (C) having a hydroxy group (also referred to as "alcohol compound (C)"), wherein at least one of the iso(thio)cyanate compound (B) or the alcohol compound (C) has a (meth)acryloyl group.

The raw material composition in the present disclosure contains the zinc catalyst (A) as a catalyst that replaces a Sn catalyst, and by reacting the iso(thio)cyanate compound (B) having an iso(thio)cyanate group and the alcohol compound (C) having a hydroxy group in the presence of the zinc catalyst (A), the monomer composition containing urethane (meth)acrylate (also referred to as "(meth)acrylate compound (D)") that is a reaction product, can be obtained.

According to the raw material composition in the present disclosure, by reacting the iso(thio)cyanate compound (B) having an iso(thio)cyanate group and the alcohol compound (C) having a hydroxy group in the presence of the zinc catalyst (A), the monomer composition containing the (meth)acrylate compound (D) can be obtained, and further a cured product formed by using the obtained monomer composition is excellent in mechanical properties such as an elastic modulus, breaking strength, breaking energy and the like. The (meth)acrylate compound (D) obtained by using the raw material composition in the present disclosure has high purity.

Hereinafter, a component contained in the raw material composition will be described.

<Zinc Catalyst (A)>

The raw material composition in the present disclosure contains the zinc catalyst (A).

The zinc catalyst (A) is a catalyst used in generation of the (meth)acrylate compound (D) (that is, a reaction of the iso(thio)cyanate compound (B) and the alcohol compound (C)).

The zinc catalyst (A) contained in the raw material composition in the present disclosure may be only one type, or may be two or more types.

As the zinc catalyst (A), a known zinc catalyst can be used.

The zinc catalyst (A) need only be a catalyst containing at least one zinc atom, for example, at least one of a sulfur-containing compound containing a sulfur atom or an oxygen-containing compound containing an oxygen atom.

Each of the sulfur-containing compound and the oxygen-containing compound is preferably at least one of a dithiocarbamate catalyst containing a zinc atom, or a zinc compound containing a zinc atom and a ring structure.

The dithiocarbamate catalyst containing a zinc atom is preferably a zinc dithiocarbamate compound. The zinc compound containing a zinc atom and a ring structure is preferably a zinc compound containing a zinc atom and an aromatic ring or a heterocycle, and more preferably a zinc compound containing a bisthiozinc skeleton (—S—Zn—S—) or a bisoxyzinc skeleton (—O—Zn—O—) and an aromatic ring or a heterocycle.

The zinc catalyst (A) is preferably at least one of a compound represented by the following formula (1) or a compound represented by the following formula (2). The compound represented by the following formula (2) may be a zinc complex.

(1)

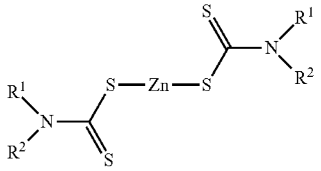

(2)

$$R^3—X^1—Zn—X^2—R^4$$

In formula (1), $R^1$ and $R^2$ are each independently a monovalent hydrocarbon group, and two $R^1$ and two $R^2$ may be the same or different, respectively. In formula (2), $X^1$ and $X^2$ are each independently an oxygen atom or a sulfur atom. $R^3$ and $R^4$ are each independently a monovalent organic group having an aromatic ring or a heterocycle, or $R^3$ and $R^4$ are organic groups that combine with each other to form a ring structure.

Examples of the monovalent hydrocarbon group in $R^1$ and $R^2$ include an alkyl group, an alkenyl group, an alkynyl group, an aryl group, an alkylaryl group, alkenylaryl group, alkynylaryl group, an arylalkyl group, an arylalkenyl group, an arylalkynyl group, and the like.

$R^1$ and $R^2$ are each independently preferably an alkyl group and an aryl group.

Examples of the alkyl group include an alkyl group having 1 to 6 carbon atoms, and more specifically, a methyl group, an ethyl group, a propyl group, and a butyl group.

Examples of the aryl group include a phenyl group.

In $R^3$ and $R^4$, examples of the aromatic ring include a benzene ring, a naphthalene ring, an anthracene ring, and a phenanthrene ring, and among them, the benzene ring is preferable.

In $R^3$ and $R^4$, examples of the heterocycle include a ring structure containing a nitrogen atom, a sulfur atom, an oxygen atom or the like, and among them, a heterocycle having aromaticity is preferable.

Specific examples of the heterocycle include a furan ring, a benzofuran ring, a pyrrole ring, an indole ring, an isoindole ring, a thiophene ring, a benzothiophene ring, an imidazole ring, a benzimidazole ring, a pyrazole ring, an indazole ring, an oxazole ring, and a benzoxazole ring, a thiazole ring, a benzothiazole ring, a pyridine ring, a quinoline ring, a pyrazine ring, a quinoxaline ring, a pyrimidine ring, a pyridazine ring, and a triazine ring, and among them, the pyridine ring and the benzothiazole ring are preferable.

$R^3$ and $R^4$ may have one or more aromatic rings and one or more heterocycles respectively, and may have a plurality of aromatic rings or a plurality of heterocycles. For example, $R^3$ and $R^4$ preferably have the benzene ring and the benzothiazole ring, respectively.

Examples of a ring structure formed by combining with each other includes the aforementioned aromatic ring and heterocycle, among them, the benzene ring is preferable. In a case in which $R^3$ and $R^4$ are combined with each other, it is preferable that the ring structure has $X^1$ and $X^2$, and a ring containing a zinc atom, and the aromatic ring or the heterocycle, and it is more preferable that the ring structure is a fused ring sharing two carbon atoms.

In $R^3$ and $R^4$, the monovalent organic group having the aromatic ring or the heterocycle and the organic group forming the ring structure may each independently have a substituent. Examples of the substituent include an alkyl group such as an alkyl group having 1 to 6 carbon atoms and an aryl group such as a phenyl group.

Specific Examples of the compound represented by the aforementioned formula (2) include compounds having the following structure.

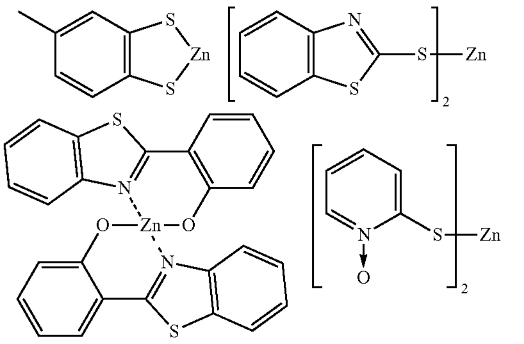

According to the raw material in the present disclosure, the content of the zinc catalyst (A) is preferably from 0.01% by mass to 1% by mass, more preferably from 0.03% by mass to 0.7% by mass, and still more preferably from 0.05% by mass to 0.5% by mass, with respect to the total content of the zinc catalyst (A), the iso(thio)cyanate compound (B) and the alcohol compound (C).

The raw material composition in the present disclosure may contain or may not contain a catalyst other than the zinc catalyst (A) (also referred to as "at least one other catalyst"). Examples of at least one other catalyst include catalysts containing a metal atom other than a zinc atom such as a tin atom, a titanium atom, a zirconium atom or the like.

According to the raw material composition in the present disclosure, the content of the at least one other catalyst may be 0.5% by mass or less, may be 0.3% by mass or less, or 0.1% by mass or less, with respect to the total content of the zinc catalyst (A), the at least one other catalyst, the iso(thio) cyanate compound (B) and the alcohol compound (C). According to the raw material composition in the present disclosure, a lower limit of the content of the at least one other catalyst is not particularly limited, and from the viewpoint of reducing a use of a heavy metal such as tin and manufacturing a cured product more excellent in mechanical properties, the lower limit may be 0% by mass.

According to the raw material composition in the present disclosure, especially, the content of a tin catalyst may be 0.5% by mass or less, may be 0.3% by mass or less, or 0.1% by mass or less, with respect to the total content of the zinc catalyst (A), the tin catalyst, the iso(thio)cyanate compound (B) and the alcohol compound (C).

(Iso(Thio)Cyanate Compound (B))

The raw material composition in the present disclosure contains the iso(thio)cyanate compound (B) having an iso (thio)cyanate group.

The iso(thio)cyanate compound (B) having an iso(thio) cyanate group contained in the raw material composition in the present disclosure may be only one type, may be two or more types.

The number of the iso(thio)cyanate group in the iso(thio) cyanate compound (B) is preferably two or three, and more preferably two.

At least one of the iso(thio)cyanate compound (B) or the alcohol compound (C) has a (meth)acryloyl group. In a case in which the alcohol compound (C) has the (meth)acryloyl group, the iso(thio)cyanate compound (B) may or may not have the (meth)acryloyl group. In a case in which the alcohol compound (C) does not have the (meth)acryloyl group, the iso(thio)cyanate compound (B) has the (meth) acryloyl group.

The iso(thio)cyanate compound (B) is preferably a isocyanate compound having two or more (more preferably two or three, and still more preferably two) isocyanate groups, and more preferably at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis (meth)acryloyloxymethyl)ethyl isocyanate and 2-isocyanatoethyl(meth)acrylate.

Among the iso(thio)cyanate compound (B), examples of the thiocyanate compounds include aliphatic polyisothiocyanate compounds such as hexamethylene diisothiocyanate, lysine diisothiocyanate methyl ester, lysine triisothiocyanate, m-xylylene diisothiocyanate, bis (isothiocyanatomethyl)sulfide, bis(isothiocyanatoethyl) sulfide, and bis(isothiocyanatoethyl)disulfide; alicyclic polyisothiocyanate compounds such as isophoron diisothiocianate, bis(isothiocyanatomethyl)cyclohexane, dicyclohexylmethane diisothiocianate, cyclohexane diisothiocianate, methylcyclohexane diisothiocianate, 2,5-bis (isothiocyanatomethyl)bicyclo-[2.2.1]-heptane, 2,6-bis (isothiocyanatomethyl)bicyclo-[2.2.1]-heptane, 3,8-bis (isothiocyanatomethyl)tricyclodecane, 3,9-bis (isothiocyanatomethyl)tricyclodecane, 4,8-bis (isothiocyanatomethyl)tricyclodecane, and 4,9-bis (isothiocyanatomethyl)tricyclodecane; aromatic polyisothiocyanate compounds such as tolylene diisocyanate, 4,4-diphenylmethane diisothiocyanate, and diphenyl disulfide-4,4-diisothiocyanate; and sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl)tetrahydrothiophene, 3,4-bis(isothiocyanatomethyl)tetrahydrothiophene, 2,5-diisothiocyanato-1,4-dithiane, 2,5-bis(isothiocyanatomethyl)-1,4-dithiane, 4,5-diisothiocyanato-1,3-dithiolane, and 4,5-bis (isothiocyanatomethyl)-1,3-dithiolane.

(Alcohol Compound (C))

The raw material composition in the present disclosure contains the alcohol compound (C) having a hydroxy group.

The alcohol compound (C) contained in the raw material composition in the present disclosure may be only one type, or may be two or more types.

At least one of the iso(thio)cyanate compound (B) or the alcohol compound (C) has a (meth)acryloyl group. In a case in which the iso(thio)cyanate compound (B) has the (meth) acryloyl group, the alcohol compound (C) may have or may not have the (meth)acryloyl group. In a case in which the iso(thio)cyanate compound (B) does not have the (meth) acryloyl group, the alcohol compound (C) has the (meth) acryloyl group.

The alcohol compound (C) is preferably at least one selected from the group consisting of 2-hydroxyethyl(meth) acrylate, 2-hydroxypropyl(meth)acrylate, 2-hydroxybutyl (meth)acrylate, 2-hydroxy-3-phenoxypropyl(meth)acrylate, 4-hydroxybutyl(meth)acrylate, 1,4-cyclohexanedimethanol mono(meth)acrylate, ethylene glycol and glycerin.

According to the raw material composition in the present disclosure, the molar ratio of the hydroxy group in the alcohol compound (C) to the iso(thio)cyanate group in the iso(thio)cyanate compound (B) (that is, molar ratio [hydroxy group/iso(thio)cyanate group]) is preferably from 0.3 to 2.0, more preferably from 0.5 to 1.5, still more preferably from 0.8 to 1.2 and further preferably from 0.9 to 1.1.

According to the raw material composition in the present disclosure, the total content of the iso(thio)cyanate compound (B) and the alcohol compound (C) is preferably 90% by mass or more, and more preferably 95% by mass or more, with respect to the total content of the zinc catalyst (A), the iso(thio)cyanate compound (B), and the alcohol compound (C).

A upper limit of the total content of the iso(thio)cyanate compound (B) and the alcohol compound (C) is appropriately determined based on the content of the zinc catalyst (A). Examples of the upper limit of the total content of the iso(thio)cyanate compound (B) and the alcohol compound (C) include 99.9% by mass, 99.7% by mass, and 99.5% by mass.

[Method of Manufacturing Raw Material Composition]

The method of manufacturing the raw material composition in the present disclosure is not particularly limited, and may include a step of mixing the zinc catalyst (A), the iso(thio)cyanate compound (B), and the alcohol compound (C).

In the method of the raw material composition, by mixing each component of the iso(thio)cyanate compound (B), and the alcohol compound (C), a reaction of the iso(thio)cyanate compound (B) and the alcohol compound (C) may partially progress. In a case in which the reaction of the iso(thio)cyanate compound (B) and the alcohol compound (C) partially progresses, the above-mentioned total content of the iso(thio)cyanate compound (B) and the alcohol compound (C) may be replaced with the total content of the iso(thio)cyanate compound (B), the alcohol compound (C) and the reaction product.

[Monomer Composition]

The monomer composition in the present disclosure contains the zinc catalyst (A), the (meth)acrylate compound (D) that is the reaction product of the iso(thio)cyanate compound (B) having an iso(thio)cyanate group, and the alcohol compound (C) having a hydroxy group. By using the monomer composition in the present disclosure, it is possible to manufacture the cured product excellent in mechanical properties such as an elastic modulus, breaking strength, breaking energy and the like.

<(Meth)Acrylate Compound (D)>

The monomer composition in the present disclosure contains the (meth)acrylate compound (D) as a monomer.

The (meth)acrylate compound (D) contained in the monomer composition in the present disclosure may be only one type or may be two or more types.

For example, it is possible to use the monomer composition in the present disclosure as a component in the curable composition mentioned later (specifically, as a source of a monomer for the curable composition mentioned later). The monomer composition itself can be used as the curable composition.

The (meth)acrylate compound (D) is the reaction product of the iso(thio)cyanate compound (B) having an iso(thio)cyanate group, and the alcohol compound (C) having a hydroxy group, and preferably the reaction product of the iso(thio)cyanate compound (B) having two or more iso(thio)cyanate groups, and the alcohol compound (C) having a hydroxy group.

In the generation reaction of the (meth)acrylate compound (D), by the reaction of the isocyanate group (that is, —N═C═O group) or the isothiocyanate group (that is, —N═C═S) in the iso(thio)cyanate compound (B), and the hydroxy group in the alcohol compound (C), an —NHC(═O)O— bond or an —NHC(═S)O— bond is formed, and the (meth)acrylate compound (D) is formed.

That is, the (meth)acrylate compound (D) is a (meth)acrylate compound containing at least one of an —NHC(═O)O— bond or an —NHC(═S)O— bond.

The monomer composition in the present disclosure may contain, other than the (meth)acrylate compound (D) (that is, reaction product), at least one of the iso(thio)cyanate compound (B) or the alcohol compound (C) as an unreacted raw material.

In the monomer composition in the present disclosure, the content of the (meth)acrylate compound (D) is preferably 50% by mass or more, more preferably 60% by mass or more, still more preferably 80% by mass or more, and particularly preferably 90% by mass or more, with respect to the total amount of the monomer composition.

In the monomer composition in the present disclosure, the total content of the (meth)acrylate compound (D), the iso(thio)cyanate compound (B) and the alcohol compound (C) is preferably 50% by mass or more, more preferably 60% by mass or more, still more preferably 80% by mass or more, and particularly preferably 90% by mass or more, with respect to the total amount of the monomer composition.

The content of the zinc catalyst (A) in the monomer composition in the present disclosure is preferably from 0.01% by mass to 1% by mass, more preferably from 0.03% by mass to 0.7% by mass, and still more preferably from 0.05% by mass to 0.5% by mass, with respect to the total content of the zinc catalyst (A), the iso(thio)cyanate compound (B), the alcohol compound (C), and the (meth)acrylate compound (D).

The content of the at least one other catalyst in the monomer composition in the present disclosure may be 0.5% by mass or less, may be 0.3% by mass or less, or may be 0.1% by mass or less, with respect to the total amount of the zinc catalyst (A), the at least one other catalyst, the iso(thio)cyanate compound (B), the alcohol compound (C), and the (meth)acrylate compound (D). According to the monomer composition in the present disclosure, a lower limit of the content of the at least one other catalyst is not particularly limited, and from the viewpoint of reducing a use of a heavy metal such as tin and manufacturing a cured product more excellent in mechanical properties, the lower limit may be 0% by mass.

According to the monomer composition in the present disclosure, especially, the content of a tin catalyst may be 0.5% by mass or less, may be 0.3% by mass or less, or 0.1% by mass or less, with respect to the total content of the zinc catalyst (A), the tin catalyst, the iso(thio)cyanate compound (B), the alcohol compound (C), and the (meth)acrylate compound (D).

<Polymerization Inhibitor>

The monomer composition in the present disclosure may contain a polymerization inhibitor.

In a case in which the monomer composition in the present disclosure contains the polymerization inhibitor, the polymerization inhibitor contained may be only one type or two or more types.

The polymerization inhibitor is not particularly limited, and examples thereof include dibutylhydroxytoluene (BHT), hydroquinone (HQ), hydroquinone monomethyl ether (MEHQ), and phenothiazine (PTZ).

The content of the polymerization inhibitor may be from 0.001% by mass to 0.5% by mass, may be from 0.002% by mass to 0.3% by mass, may be from 0.005% by mass to 0.3% by mass, or may be from 0.01% by mass to 0.2% by mass, with respect to the total amount of the zinc catalyst (A), the iso(thio)cyanate compound (B), the alcohol compound (C), and the (meth)acrylate compound (D).

<Other Monomer>

The monomer composition in the present disclosure may contain at least one other monomer in addition to the (meth)acrylate compound (D), and the iso(thio)cyanate compound (B) and the alcohol compound (C) that are the raw materials thereof.

Examples of the at least one other monomer include a (meth)acrylate other than the (meth)acrylate compound (D), the iso(thio)cyanate compound (B) or the alcohol compound (C) (hereinafter, also referred to as "(meth)acrylate compound (E)").

Examples of the (meth)acrylate compound (E) include neopentyldi (meth)acrylate, 1,4-butanediol di(meth)acrylate, 1,6-hexanediol di(meth)acrylate, and 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, propylene oxide-modified bisphenol A di(meth)acrylate.

In a case in which the monomer composition in the present disclosure contains at least one other monomer (for example, (meth)acrylate compound (E)), the content of the at least one other monomer is preferably from 1% by mass to 70% by mass, more preferably from 5% by mass to 50% by mass, still more preferably from 10% by mass to 40% by mass, and further more preferably from 20% by mass to 40% by mass, with respect to the total content of the iso(thio)cyanate compound (B), the alcohol compound (C), the (meth)acrylate compound (D), and the at least one other monomer (however, a compound not having a (meth)acryloyl group is excluded).

<Other Component>

The monomer composition in the present disclosure may contain at least one other component other than the above-mentioned components.

Examples of the at least one other component that may be contained in the monomer composition in the present disclosure, include components in the curable composition mentioned later.

[Method of Manufacturing Monomer Composition]

The method of manufacturing a monomer composition in the present disclosure includes a step (hereinafter, also referred to as "mixing step") of mixing the zinc catalyst (A), the iso(thio)cyanate compound (B) having an iso(thio)cyanate group, and the alcohol compound (C) having a hydroxy group, in which at least one of the iso(thio)cyanate compound (B) or the alcohol compound (C) has a (meth)acryloyl group.

The method of manufacturing a monomer composition in the present disclosure may include other steps if necessary.

In the mixing step, by mixing each component of the zinc catalyst (A), the iso(thio)cyanate compound (B) having an iso(thio)cyanate group, and the alcohol compound (C), a reaction of the iso(thio)cyanate compound (B) and the alcohol compound (C) progress, and the (meth)acrylate compound (D) that is the reaction product is produced. As a result, it is possible to manufacture the (meth)acrylate compound (D) by using a catalyst that replaces a Sn catalyst, and it is possible to manufacture the cured product excellent in mechanical properties such as an elastic modulus, breaking strength, breaking energy and the like.

In the mixing step, an aspect of mixing each component is not particularly limited.

As the aspect of mixing each component, it is preferable that the zinc-based catalyst (A) is mixed with one of the iso(thio)cyanate compound (B) and the alcohol compound (C) to prepare a composition, and the other of the iso(thio)cyanate compound (B) and the alcohol compound (C) is added to and mixed with the obtained composition. At this time, the other of the iso(thio)cyanate compound (B) and the alcohol compound (C) may be gradually mixed by dropping or the like.

As the aspect of mixing each component, it is more preferable that one of the iso(thio)cyanate compound (B) and the alcohol compound (C) has a (meth)acryloyl group, the other does not have a (meth)acryloyl group, and each component is mixed as follows. Specifically, the more preferable aspect is that the zinc catalyst (A) is mixed with the compound that is one of the iso(thio)cyanate compound (B) and the alcohol compound (C) and does not have a (meth)acryloyl group, to prepare a composition, and the compound that is the other of the iso(thio)cyanate compound (B) and the alcohol compound (C) and has a (meth)acryloyl group is added to and mixed with the obtained composition. This tends to allow the reaction between the iso(thio)cyanate compound (B) and the alcohol compound (C) to progress suitably while suppressing the polymerization reaction of the (meth)acryloyl group.

The reaction temperature of the above described reaction in the mixing step is preferably from 40° C. to 90° C., more preferably from 50° C. to 90° C., and still more preferably from 60° C. to 90° C.

The reaction time of the above described reaction in the mixing step is preferably 1 hour or more, more preferably 2 hours or more, and still more preferably 3 hours or more, from the viewpoint of further advancing the reaction between the iso(thio)cyanate compound (B) and the alcohol compound (C).

The reaction time is preferably 30 hours or less, more preferably 25 hours or less, and still more preferably 20 hours or less, from the viewpoint of suppressing decomposition and polymerization of the (meth)acrylate compound (D), a side reaction between iso(thio)cyanate compounds (B) and the like.

The preferable range of the amount used of the zinc catalyst (A) in the mixing step is the same as the content of the zinc catalyst (A) in the raw material in the present disclosure.

Preferable ranges of the molar ratio [hydroxy group/iso(thio)cyanate group] and the total amount of the iso(thio)cyanate compound (B) and the alcohol compound (C) in the mixing step are the same as those of the molar ratio [hydroxy group/iso(thio)cyanate group] and the total content of the iso(thio)cyanate compound (B) and the alcohol compound (C) in the raw material in the present disclosure.

In the mixing step, not only each component of the zinc catalyst (A), the iso(thio)cyanate compound (B), and the alcohol compound (C) but also at least one other component may be added and mixed.

The at least one other component is preferably a polymerization inhibitor. For the polymerization inhibitor, the section "Monomer Composition" can be referred to as appropriate.

In the mixing step, in a case in which each component was mixed by adding the polymerization inhibitor, the polymerization of the alcohol compound (C) can be further suppressed, and the reaction between the iso(thio)cyanate compound (B) and the alcohol compound (C) can progress more effectively.

The amount used of the polymerization inhibitor may be from 0.001% by mass to 0.5% by mass, may be from 0.002% by mass to 0.3% by mass, or may be from 0.005% by mass to 0.3% by mass, with respect to the total amount used of the zinc catalyst (A), the iso(thio)cyanate compound (B), and the alcohol compound (C).

[Curable Composition]

The curable composition in the present disclosure contains the above-mentioned monomer composition in the present disclosure.

That is, the curable composition in the present disclosure contains each component in the above-mentioned monomer composition in the present disclosure.

The curable composition in the present disclosure may consist of the above-mentioned monomer composition in the present disclosure (that is, the monomer composition itself in the present disclosure).

The curable composition in the present disclosure is suitably used in a manufacture of a cured product (for example, a molded body mentioned later). Herein, the cured product means a product formed by curing the curable composition in the present disclosure.

The curing of the curable composition in the present disclosure is achieved by the polymerization of the contained monomers.

Examples of methods of curing the curable composition in the present disclosure include a method of polymerizing the monomer in the curable composition at room temperature, a method of thermally polymerizing the monomer in the curable composition, and a method of photopolymerizing the monomer in the curable composition.

The curable composition in the present disclosure is excellent in mechanical properties (for example, an elastic modulus, breaking strength, breaking energy) when made into the cured product.

It is considered that the above-mentioned (meth)acrylate compound (D) (that is, the (meth)acrylate compound (D) containing a urethane bond) as a monomer contributes to such effects.

The content of the monomer composition in the curable composition in the present disclosure is preferably 10% by mass or more, more preferably 20% by mass or more, and still more preferably 30% by mass or more, with respect to the total amount of the curable composition.

The content of the monomer composition in the curable composition in the present disclosure may be 100% by mass, may be 80% by mass or less, or may be 60% mass or less, 50% by mass or less or the like, with respect to the total amount of the curable composition.

<Polymerization Initiator>

The curable composition in the present disclosure preferably contains a polymerization initiator.

In a case in which the curable composition in the present disclosure contains the polymerization initiator, the polymerization initiator contained may be only one type or two or more types.

In a case in which the curable composition in the present disclosure contains the polymerization initiator, in the process of curing the curable composition, the polymerization of the monomer (that is, the (meth)acrylate compound (D) and other monomers contained if necessary; the same applies hereinafter) can be further promoted.

When performing room temperature polymerization as monomer polymerization, as the polymerization initiator, for example, a redox-based polymerization initiator formed by a combination of an oxidizing agent and a reducing agent is preferable.

In a case in which the redox-based polymerization initiator is used, for example, the oxidizing agent and the reducing agent in separately packaged form may be prepared, and both may be mixed just before use.

The oxidizing agent is not particularly limited, and examples thereof include organic peroxides such as diacyl peroxides (benzoyl peroxide, and the like), peroxyesters (t-butyl peroxybenzoate, and the like), dialkyl peroxides (dicumyl peroxide, and the like), peroxyketars (1,1-bis(t-butyl peroxy)-3,3,5-trimethylcyclohexane, and the like), ketone peroxides (methyl ethyl ketone peroxide, and the like), and hydroperoxides (t-butyl hydroperoxide, and the like)

The reducing agent is not particularly limited, and usually a tertiary amine (N, N-dimethylaniline, and the like) is used as the reducing agent.

In addition to these organic peroxide/amine-based polymerization initiators, redox-based polymerization initiators such as cumenehydroperoxide/thiourea-based, ascorbic acid/Cu' salt-based, and organic peroxide/amine/sulfinic acid (or salt thereof)-based can be used.

As the polymerization initiator, tributylborane, organic sulfinic acid and the like are also preferably used.

When performing thermal polymerization by heating, the polymerization initiators such as peroxides and azo compounds are preferable.

The peroxide is not particularly limited, and example thereof include benzoyl peroxide, t-butyl hydroperoxide, and cumene hydroperoxide.

The azo compound is not particularly limited, and example thereof include azobisisobutyronitrile.

Polymerization initiators in a case in which photopolymerization by visible light irradiation is performed as monomer polymerization (hereinafter, also referred to as "photopolymerization initiator") are preferably redox-based initiators such as α-diketone/tertiary amine, α-diketone/aldehyde, α-diketone/mercaptan and the like.

Photopolymerization initiator is not particularly limited, and examples thereof include α-diketone/reducing agent, ketal/reducing agent, and thioxanthone/reducing agent.

Examples of the α-diketone include camphorquinone.

Examples of the ketal include benzyldimethyl ketal.

Examples of the thioxanthone include 2-chlorothioxanthone.

Examples of the reducing agent include tertiary amines (Michler's ketone and the like), aldehydes (citronellal and the like), and compounds containing a thiol group (2-mercaptobenzoxazole and the like).

Polymerization initiators such as α-diketone/organic peroxide/reducing agent-based polymerization initiators prepared by adding the organic peroxide to these redox-based polymerization initiators are also preferably used.

In a case in which photopolymerization by ultraviolet irradiation is performed, the photopolymerization initiators such as benzoin alkyl ether, benzyl dimethyl ketal and the like are preferable. The photopolymerization initiators of (bis)acylphosphine oxides are also preferably used.

Examples of the (bis)acylphosphine oxides include acylphosphine oxides (2,4,6-trimethylbenzoyldiphenylphosphine oxide and the like), bisacylphosphine oxides (bis-(2,6-dichlorobenzoyl)phenylphosphine oxide and the like) and the like.

The photopolymerization initiators of these (bis) acylphosphine oxides may be used singly or in combination with reducing agents such as various amines, aldehydes, mercaptans and sulfinates.

The photopolymerization initiators of these (bis) acylphosphine oxides may be used in combination with the above described visible light photopolymerization initiators.

For example, the polymerization initiator may be used with reference to International Publication No. 2019/107323, International Publication No. 2020/040141 and the like.

The content of the polymerization initiator is preferably from 0.01% by mass to 20% by mass, and more preferably from 0.1% by mass to 5% by mass, with respect to the total amount of the monomer contained in the curable composition.

<Fillers>

The curable composition in the present disclosure may contain fillers.

In a case in which the curable composition in the present disclosure contains the fillers, the fillers contained may be only one type, or may be two or more types.

In a case in which the curable composition in the present disclosure contains the fillers, mechanical properties when made into the cured product are more improved.

Fillers are usually roughly classified into organic fillers and inorganic fillers.

Examples of organic fillers include fine powders of polymethyl methacrylate.

Examples of inorganic fillers include fine powders of various glasses (mainly silicon dioxide, and if necessary, containing an oxide of a heavy metal, boron, aluminum or the like), various ceramics, diatomaceous earth, kaolin, clay minerals (montmorillonite, and the like), activated clay, synthetic zeolite, mica, calcium fluoride, ytterbium fluoride, calcium phosphate, barium sulfate, zirconium dioxide, titanium dioxide, and hydroxyapatite.

Specific examples of the inorganic fillers include barium borosilicate glasses, strontium boroaluminosilicate glasses, lantern glasses, fluoroaluminosilicate glasses, and boroaluminosilicate glasses.

For example, the fillers may be used with reference to International Publication No. 2019/107323, International Publication No. 2020/040141 and the like.

The content of the fillers is preferably from 10 parts by mass to 2000 parts by mass, more preferably from 50 parts by mass to 1000 parts by mass, and still more preferably from 100 parts by mass to 600 parts by mass, in a case in which the total amount of the monomer in the curable composition is 100 parts by mass.

<Other Component>

The curable composition in the present disclosure may contain at least one other component other than the above-mentioned components.

Examples of the at least one other component include pigments, dyes, bactericides, disinfectants, stabilizers, preservatives and the like.

<Preferred Uses>

Uses of the curable composition in the present disclosure is not particularly limited.

The curable composition in the present disclosure, for example, may be used as a coating material, a composition for forming a coating film, composition for a dental material and the like.

Since the curable composition in the present disclosure can form the cured product excellent in mechanical properties, especially, it is preferable that the curable composition is the composition for a dental material.

Herein, the composition for a dental material means a composition for a dental material itself, a cured product of the composition for a dental material (for example, the molded body described later), or a composition in which a further processed product of the above described cured product can be used as the dental material.

Examples of the dental material include a dental restorative material, a denture base resin, a denture base lining material, an impression material, a joint wearing material (resin cement, resin-added glass ionomer cement and the like), a dental adhesive (an orthodontic adhesive, a cavity coating adhesive and the like), a tooth fissure sealant, resin block for CAD/CAM, temporary crown, and an artificial tooth material.

Examples of the dental restorative material include a composite resin for a crown, a composite resin for filling a caries cavity, a composite resin for abutment construction, and a composite resin for filling restoration.

<One Example of Manufacturing Method>

A manufacturing method of manufacturing the curable composition in the present disclosure is not particularly limited.

Hereinafter, one example of a method of manufacturing the curable composition in the present disclosure will be described.

For example, the method of manufacturing the curable composition in the present disclosure includes a step of preparing the monomer composition in the present disclosure, and a step of mixing the monomer composition and at least one other component (for example, polymerization initiator, filler and the like).

The method of manufacturing the curable composition in the present disclosure may include another step as necessary.

[Molded Body]

The molded body in the present disclosure is a cured product of the above described curable composition in the present disclosure.

Accordingly, the molded body in the present disclosure is excellent in mechanical properties.

The molded body is manufactured, for example, by molding the curable composition in the present disclosure into a desired shape and then curing it.

An example of a method of curing the curable composition in the present disclosure is as described above.

EXAMPLES

Hereinafter, examples in the present disclosure will be shown. The present disclosure is not limited to the following examples.

The abbreviations of the compounds used in the examples of the present invention are shown below.

HEMA: 2-hydroxyethyl methacrylate

TMHDI: Mixture of 2,2,4-trimethylhexamethylene diisocyanate and 2,4,4-trimethylhexamethylene diisocyanate MOI: 2-isocyanatoethyl methacrylate GLY: Glycerin Zn-1: Zinc dimethyldithiocarbamate Zn-2: Zinc di ethyldithiocarbamate
Zn-3: Zinc dibutyldithiocarbamate
Zn-4: Zinc N-ethyl-N-phenyldithiocarbamate
Zn-5: (Toluene-3,4-dithiolate)zinc
Zn-6: Bis [2-(2-benzothiazolyl)phenolato]zinc
DBTDL: dibutyltin dilaurate
Ti-1: Titanium tetra-2-ethylhexoside
Ti-2: Titanium diisopropoxybis(ethylacetacetate)
Zr-1: Zirconium tetraacetyl acetate
Zr-2: Zirconium dibutoxybis(ethylacetoacetate)
BHT: Dibutylhydroxytoluene
CQ: Camphorquinone
DMAB2-BE: 2-butoxyethyl 4-dimethylaminobenzoate
3G: Triethylene glycol dimethacrylate

[Method of Measuring HPLC]

The HPLC chart spectrum of urethane dimethacrylate obtained in each example was measured using an HPLC apparatus: LC-20AT manufactured by Shimadzu Corporation.

After dissolving the urethane dimethacrylate obtained in each example in $CH_3CN$, the urethane dimethacrylate was measured with an eluent of $CH_3CN/H_2O=90/10$.

[Method of Bending Test]

The method of a bending test in the examples and the comparative examples in the present invention is shown below.

(Preparation of Test Piece for Bending Test)

The monomer composition for a dental material was prepared by adding 0.05 parts by mass of CQ and 0.05 parts by mass of DMAB2-BE to 10 parts by mass of the monomer composition obtained in each example or comparative example, stirring the mixture at room temperature until uniform, further adding 15 parts by mass of silica glass (Fusedex-X (Tatsumori Co., Ltd.)), stirring the mixture using a mortar until uniform, and then defoaming the mixture. The obtained composition for a dental material was placed in a stainless steel mold of 2 mm×$2_{mm}$×25 mm, and light was irradiated for 3 minutes on each side, that is, for 6 minutes on both sides using a visible light irradiation device (Solidayite V manufactured by Shofu Inc.). Further, the test piece taken out from the stainless steel mold was heat-treated in an oven at 130° C. for 2 hours. After cooling the cured product taken out from the oven to room temperature, the cured product was immersed in distilled water in a sealable sample bottle and held at 37° C. for 24 hours. The cured product after immersed was used as the test piece (test piece for bending test).

(Bending Test)

A three-point bending test was performed by using the test piece prepared by the above method and a testing machine (Autograph EZ-S manufactured by Shimadzu Corporation) at a distance between fulcrums of 20 mm and a crosshead speed of 1 mm/min.

[Method of Measuring Viscosity]

The viscosity of the examples and the comparative examples in the present invention was measured by using E-type viscometer (TVE-22H manufactured by Toki Sangyo Co., Ltd) with the temperature of the monomer compositions controlled to 65° C.

The viscosity of the examples and the comparative examples in the present invention is viscosity immediately after preparing the monomer compositions.

[Method of Measuring Refractive Index]

The refractive index of the examples and the comparative examples in the present invention was measured by using abbe type full digital refractive index meter (Abbemat 550 manufactured by Anton Paar) with the temperature of the monomer compositions controlled to 25° C.

Example 1

0.05 parts by mass of Zn-1, 0.025 parts by mass of BHT, and 22.34 parts by mass of TMHDI were charged in a 100 mL 4-neck flask equipped with a well-dried stirring blade and a thermometer, after dissolving them to make a homogeneous solution, the temperature of this solution was raised to 80° C., and further 27.66 parts by mass of HEMA was added dropwise to this solution over 1 hour. Since the internal temperature increased due to the heat of reaction during the dropping, the dropping amount was controlled so as to be 90° C. or lower. After dropping the entire amount of HEMA, the reaction was carried out for 4.5 hours while maintaining the reaction temperature at 90° C. At this time, the progress of the reaction was followed by HPLC analysis to confirm the end point of the reaction. By discharging the product from the reactor, 50 g of urethane dimethacrylate (A-1) was obtained. HPLC purity was 97.1 area %. The viscosity at 65° C. was 180 mPa·s. The refractive index at 25° C. was 1.4839. 12.0 parts by mass of the obtained urethane dimethacrylate (A-1) and 3.0 parts by mass of 3G were placed in a container and stirred at 50° C. until uniform to obtain a monomer composition (1). By using the obtained monomer composition (1), a composition (1) for a dental material, and the test piece (test piece for bending test) were obtained according to the methods described in the sections of (Preparation of Test Piece for Bending Test) and (Bending Test). When the bending test was carried out, the elastic modulus was 7760 MPa, the breaking strength was 179 MPa, and the breaking energy was 32 mJ.

Examples 2 to 6

50 g of urethane dimethacrylates (A-2) to (A-6) were obtained in the same manner as Example 1 except that each catalyst was changed to the compound shown in Table 1, and reaction time was changed to 2.5 hours in Example 2, and 8 hours in Examples 3 and 4. The HPLC purity, the viscosity at 65° C. and the refractive index at 25° C. are shown in Table 1. Monomer compositions (2) to (6) were obtained in the same manner as Example 1 except that urethane dimethacrylate (A-1) was respectively changed to urethane dimethacrylates (A-2) to (A-6). By using the obtained monomer compositions (2) to (6), compositions (2) to (6) for a dental material, and the test pieces (test pieces for bending test) were obtained according to the methods described in the sections of (Preparation of Test Piece for Bending Test) and (Bending Test), and then the bending test was carried out. The elastic modulus, the breaking strength, and the breaking energy in Examples 2 to 6 are shown in Table 1.

Example 7

0.05 parts by mass of Zn-1, 0.05 parts by mass of BHT, and 8.26 parts by mass of GLY were charged in a 100 mL 4-neck flask equipped with a well-dried stirring blade and a thermometer, after dissolving them to make a homogeneous solution, the temperature of this solution was raised to 80° C., and further 41.74 parts by mass of MOI was added dropwise to this solution over 1 hour. Since the internal temperature increased due to the heat of reaction during the dropping, the dropping amount was controlled so as to be 90° C. or lower. After dropping the entire amount of MOI, the reaction was carried out for 16 hours while maintaining the reaction temperature at 90° C. At this time, the progress of the reaction was followed by HPLC analysis to confirm the end point of the reaction. By discharging the product from the reactor, 50 g of urethane dimethacrylate (A-7) was obtained. HPLC purity was 90.8 area %. 6.0 parts by mass of the obtained urethane dimethacrylate (A-7) and 9.0 parts by mass of 3G were placed in a container and stirred at 50° C. until uniform to obtain a monomer composition (7). By using the obtained monomer composition (7), a composition (7) for a dental material, and the test piece (test piece for bending test) were obtained according to the methods described in the sections of (Preparation of Test Piece for Bending Test) and (Bending Test). When the bending test was carried out, the elastic modulus was 7280 MPa, the breaking strength was 133 MPa, and the breaking energy was 16 mJ.

Examples 8 to 12

50 g of urethane dimethacrylates (A-8) to (A-12) were obtained in the same manner as Example 7 except that each catalyst was changed to the compound shown in Table 2, and reaction time was changed to 12 hours in Example 8, 13 hours in Example 9, and 11 hours in Example 10. The HPLC purity is shown in Table 2. Monomer compositions (8) to (12) were obtained in the same manner as Example 7 except that urethane dimethacrylate (A-7) was respectively changed to urethane dimethacrylates (A-8) to (A-12). By using the obtained monomer compositions (8) to (12), compositions (8) to (12) for a dental material, and the test pieces (test pieces for bending test) were obtained according to the methods described in the sections of (Preparation of Test Piece for Bending Test) and (Bending Test), and then the bending test was carried out. The elastic modulus, the breaking strength, and the breaking energy in Examples 8 to 12 are shown in Table 2.

Comparative Example 1

0.05 parts by mass of DBTDL, 0.025 parts by mass of BHT, and 22.34 parts by mass of TMHDI were charged in a 100 mL 4-neck flask equipped with a well-dried stirring blade and a thermometer, after dissolving them to make a homogeneous solution, the temperature of this solution was raised to 80° C., and further 27.66 parts by mass of HEMA was added dropwise to this solution over 1 hour. Since the internal temperature increased due to the heat of reaction during the dropping, the dropping amount was controlled so as to be 90° C. or lower. After dropping the entire amount of HEMA, the reaction was carried out for 3 hours while maintaining the reaction temperature at 90° C. At this time, the progress of the reaction was followed by HPLC analysis to confirm the end point of the reaction. By discharging the product from the reactor, 50 g of urethane dimethacrylate (A-13) was obtained. HPLC purity was 98.2 area %. The viscosity at 65° C. was 170 mPa·s. The refractive index at 25° C. was 1.4836. 12.0 parts by mass of the obtained urethane dimethacrylate (A-13) and 3.0 parts by mass of 3G were placed in a container and stirred at 50° C. until uniform to obtain a monomer composition (13). By using the obtained monomer composition (13), a composition (13) for a dental material, and the test piece (test piece for bending test) were obtained according to the methods described in the sections of (Preparation of Test Piece for Bending Test) and (Bending Test). When the bending test was carried out, the elastic modulus was 7960 MPa, the breaking strength was 178 MPa, and the breaking energy was 30 mJ.

Comparative Examples 2 to 5

50 g of urethane dimethacrylates (A-14) to (A-17) were obtained in the same manner as Comparative Example 1 except that each catalyst was changed to the compound shown in Table 1, and reaction time was changed to 5 hours in Comparative Example 3, 18 hours in Comparative Example 4, and 18 hours in Comparative Example 5. The HPLC purity, the viscosity at 65° C. and the refractive index at 25° C. are shown in Table 1. Monomer compositions (14) to (17) were obtained in the same manner as Comparative Example 1 except that urethane dimethacrylate (A-13) was respectively changed to urethane dimethacrylates (A-14) to (A-17). By using the obtained monomer compositions (14) to (17), compositions (14) to (17) for a dental material, and the test pieces (test pieces for bending test) were obtained according to the methods described in the sections of (Preparation of Test Piece for Bending Test) and (Bending Test), and then the bending test was carried out. The elastic modulus, the breaking strength, and the breaking energy in Comparative Examples 2 to 5 are shown in Table 1.

Comparative Example 6

0.05 parts by mass of DBTDL, 0.025 parts by mass of BHT, and 8.26 parts by mass of GLY were charged in a 100 mL 4-neck flask equipped with a well-dried stirring blade and a thermometer, after dissolving them to make a homogeneous solution, the temperature of this solution was raised to 80° C., and further 41.74 parts by mass of MOI was added dropwise to this solution over 1 hour. Since the internal temperature increased due to the heat of reaction during the dropping, the dropping amount was controlled so as to be 90° C. or lower. After dropping the entire amount of MOI, the reaction was carried out for 6 hours while maintaining the reaction temperature at 90° C. At this time, the progress of the reaction was followed by HPLC analysis to confirm the end point of the reaction. By discharging the product from the reactor, 50 g of urethane dimethacrylate (A-18) was obtained. HPLC purity was 92.2 area %. 6.0 parts by mass of the obtained urethane dimethacrylate (A-18) and 9.0 parts by mass of 3G were placed in a container and stirred at 50° C. until uniform to obtain a monomer composition (18). By using the obtained monomer composition (18), a composition (18) for a dental material, and the test piece (test piece for bending test) were obtained according to the methods described in the sections of (Preparation of Test Piece for Bending Test) and (Bending Test). When the bending test was carried out, the elastic modulus was 7620 MPa, the breaking strength was 135 MPa, and the breaking energy was 13 mJ.

Comparative Examples 7 to 10

50 g of urethane dimethacrylates (A-19) to (A-22) were obtained in the same manner as Comparative Example 6 except that each catalyst was changed to the compound shown in Table 2, and reaction time was changed to 8 hours in Comparative Example 8, 24 hours in Comparative Example 9, and 22 hours in Comparative Example 10. The HPLC purity is shown in Table 2. Monomer compositions (19) to (22) were obtained in the same manner as Comparative Example 6 except that urethane dimethacrylate (A-18) was respectively changed to urethane dimethacrylates (A-19) to (A-22). By using the obtained monomer compositions (19) to (22), compositions (19) to (22) for a dental material, and the test pieces (test pieces for bending test) were obtained according to the methods described in the sections of (Preparation of Test Piece for Bending Test) and (Bending Test), and then the bending test was carried out. The elastic modulus, the breaking strength, and the breaking energy in Comparative Examples 7 to 10 are shown in Table 2.

The disclosures of Japanese Patent Application No. 2019-150510 filed on Aug. 20, 2019 is hereby incorporated by reference in its entirety.

All the documents, patent applications and technical standards that are described in the present specification are hereby incorporated by reference to the same extent as if each individual document, patent application or technical standard is concretely and individually described to be incorporated by reference.

TABLE 1

| | | Monomer synthesis | | | Physical properties of monomer composition | | | Physical properties of cured product | | |
|---|---|---|---|---|---|---|---|---|---|---|
| | | Isocyanate compound | Alcohol compound | Catalyst | Viscosity [mPa · s] | Refractive index | HPLC [area %] | Elastic modulus [MPa] | Breaking strength [MPa] | Breaking energy [mJ] |
| Example | 1 | TMHDI | HEMA | Zn-1 | 180 | 1.4839 | 97.1 | 7760 | 179 | 32 |
| | 2 | TMHDI | HEMA | Zn-2 | 180 | 1.4840 | 97.4 | 7750 | 181 | 30 |
| | 3 | TMHDI | HEMA | Zn-3 | 180 | 1.4839 | 96.2 | 7970 | 183 | 31 |
| | 4 | TMHDI | HEMA | Zn-4 | 180 | 1.4841 | 97.3 | 7810 | 183 | 32 |
| | 5 | TMHDI | HEMA | Zn-5 | 170 | 1.4837 | 96.5 | 7750 | 182 | 33 |
| | 6 | TMHDI | HEMA | Zn-6 | 180 | 1.4835 | 95.1 | 7810 | 184 | 33 |
| Comparative Example | 1 | TMHDI | HEMA | DBTDL | 170 | 1.4836 | 98.2 | 7960 | 178 | 30 |
| | 2 | TMHDI | HEMA | Ti-1 | 390 | 1.4863 | 20.3 | 5720 | 113 | 22 |
| | 3 | TMHDI | HEMA | Ti-2 | 260 | 1.4858 | 58.5 | 6340 | 135 | 25 |
| | 4 | TMHDI | HEMA | Zr-1 | 230 | 1.4852 | 76.4 | 7020 | 148 | 26 |
| | 5 | TMHDI | HEMA | Zr-2 | 220 | 1.4851 | 78.3 | 7130 | 151 | 26 |
| Example | 7 | MOI | GLY | Zn-1 | — | — | 90.8 | 7280 | 133 | 16 |
| | 8 | MOI | GLY | Zn-2 | — | — | 90.6 | 7630 | 139 | 17 |
| | 9 | MOI | GLY | Zn-3 | — | — | 93.7 | 7680 | 137 | 16 |
| | 10 | MOI | GLY | Zn-4 | — | — | 90.1 | 7430 | 136 | 15 |
| | 11 | MOI | GLY | Zn-5 | — | — | 91.2 | 7580 | 138 | 15 |
| | 12 | MOI | GLY | Zn-6 | — | — | 92.1 | 7460 | 136 | 15 |
| Comparative Example | 6 | MOI | GLY | DBTDL | — | — | 92.2 | 7620 | 135 | 13 |
| | 7 | MOI | GLY | Ti-1 | — | — | 50.3 | 5100 | 111 | 14 |
| | 8 | MOI | GLY | Ti-2 | — | — | 71.9 | 6850 | 120 | 9 |
| | 9 | MOI | GLY | Zr-1 | — | — | 62.1 | 6160 | 101 | 8 |
| | 10 | MOI | GLY | Zr-2 | — | — | 68.1 | 6380 | 118 | 10 |

As shown in Table 1, physical properties of the monomer compositions and the cured products in Examples 1 to 6 were on the same level with those in Comparative Example 1. Therefore, it was confirmed that as the catalysts for forming urethane dimethacrylate, the zinc catalysts were possible to use in place of the tin catalysts.

Further, as shown in Table 1, the purity of urethane dimethacrylates in Comparative Examples 2 to 5 used in the titanium catalyst or the zirconium catalyst as the catalyst for forming urethane dimethacrylate was lower than that in Examples 1 to 6. Physical properties of the cured products in Comparative Examples 2 to 5 were inferior to those in Examples 1 to 6.

As shown in Table 2, physical properties of the monomer compositions and the cured products in Examples 7 to 12 were on the same level with those in Comparative Example 6. Therefore, it was confirmed that as the catalysts for forming urethane dimethacrylate, the zinc catalysts were possible to use in place of the tin catalysts.

Further, as shown in Table 2, the purity of urethane dimethacrylates in Comparative Examples 7 to 10 used in the titanium catalyst or the zirconium catalyst as the catalyst for forming urethane dimethacrylate was lower than that in Examples 7 to 12. Physical properties of the cured products in Comparative Examples 7 to 10 were inferior to those in Examples 7 to 12.

In Examples 7 to 12 and Comparative Examples 6 to 10, since the monomer compositions were solid, the measurement of viscosity and refractive index was omitted.

The invention claimed is:

1. A method of manufacturing a monomer composition, comprising mixing a zinc catalyst (A), an iso(thio)cyanate compound (B) having an iso(thio)cyanate group, and an alcohol compound (C) having a hydroxy group, and reacting the iso(thio)cyanate compound (B) having an iso(thio)cyanate group and the alcohol compound (C) having a hydroxy group in the presence of the zinc catalyst (A) to obtain the monomer composition containing urethane (meth)acrylate that is a reaction product, wherein at least one of the iso(thio)cyanate compound (B) or the alcohol compound (C) has a (meth) acryloyl group and in a case in which the iso(thio) cyanate compound (B) does not have the (meth) acryloyl group, the alcohol compound (C) consists of a compound that has the (meth)acryloyl group, and wherein the alcohol compound (C) is at least one selected from the group consisting of 2-hydroxyethyl(meth) acrylate, 2-hydroxypropyl(meth)acrylate, 2-hydroxybutyl(meth)acrylate, 2-hydroxy-3-phenoxypropyl (meth)acrylate, 4-hydroxybutyl(meth)acrylate, and 1,4-cyclohexanedimethanol mono(meth)acrylate.

2. The method of manufacturing a monomer composition according to claim 1, wherein the zinc catalyst (A) is at least one of a sulfur-containing compound containing a sulfur atom or an oxygen-containing compound containing an oxygen atom.

3. The method of manufacturing a monomer composition according to claim 1, wherein the zinc catalyst (A) is at least one of a compound represented by the following formula (1) or a compound represented by the following formula (2):

(1)

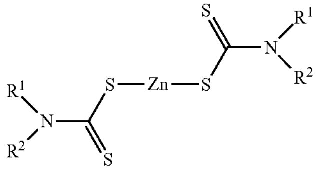

(2)

$$R^3—X^1—Zn—X^2—R^4$$

wherein, in formula (1), $R^1$ and $R^2$ are each independently a monovalent hydrocarbon group, and two $R^1$ and two $R^2$ may be the same or different, respectively, and wherein, in formula (2), $X^1$ and $X^2$ are each independently an oxygen atom or a sulfur atom, $R^3$ and $R^4$ are each independently a monovalent organic group having an aromatic ring or a heterocycle, or $R^3$ and $R^4$ are organic groups that combine with each other to form a ring structure.

4. The method of manufacturing a monomer composition according to claim 1, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth)acrylate.

5. A raw material composition, comprising: a zinc catalyst (A), an iso(thio)cyanate compound (B) having an iso(thio)cyanate group, and an alcohol compound (C) having a hydroxy group, wherein at least one of the iso(thio)cyanate compound (B) or the alcohol compound (C) has a (meth)acryloyl group, wherein a molar ratio of the hydroxy group in the alcohol compound (C) to the iso(thio)cyanate group in the iso(thio)cyanate compound (B) (that is, molar ratio [hydroxy group/iso(thio)cyanate group]) is from 0.8 to 1.2 and in a case in which the iso(thio)cyanate compound (B) does not have the (meth)acryloyl group, the alcohol compound (C) consists of a compound that has the (meth)acryloyl group, and wherein the alcohol compound (C) is at least one selected from the group consisting of 2-hydroxyethyl(meth)acrylate, 2-hydroxypropyl(meth)acrylate, 2-hydroxybutyl(meth)acrylate, 2-hydroxy-3-phenoxypropyl(meth)acrylate, 4-hydroxybutyl(meth)acrylate, and 1,4-cyclohexanedimethanol mono(meth)acrylate.

6. A monomer composition containing a zinc catalyst (A) and a (meth)acrylate compound (D) that is a reaction product of an iso(thio)cyanate compound (B) having an iso(thio)cyanate group, and an alcohol compound (C) having a hydroxy group, wherein a molar ratio of the hydroxy group in the alcohol compound (C) to the iso(thio)cyanate group in the iso(thio)cyanate compound (B) (that is, molar ratio [hydroxy group/iso(thio)cyanate group]) is from 0.8 to 1.2 and in a case in which the iso(thio)cyanate compound (B) does not have the (meth)acryloyl group, the alcohol compound (C) consists of a compound that has the (meth)acryloyl group, and wherein the alcohol compound (C) is at least one selected from the group consisting of 2-hydroxyethyl(meth)acrylate, 2-hydroxypropyl(meth)acrylate, 2-hydroxybutyl(meth)acrylate, 2-hydroxy-3-phenoxypropyl(meth)acrylate, 4-hydroxybutyl(meth)acrylate, and 1,4-cyclohexanedimethanol mono(meth)acrylate.

7. The monomer composition according to claim 6, wherein the zinc catalyst (A) is at least one of a compound represented by the following formula (1) or a compound represented by the following formula (2):

(1)

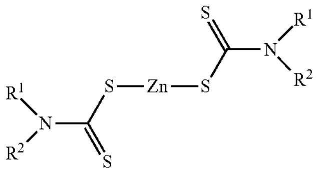

(2)

$$R^3—X^1—Zn—X^2—R^4$$

wherein, in formula (1), $R^1$ and $R^2$ are each independently a monovalent hydrocarbon group, and two $R^1$ and two $R^2$ may be the same or different, respectively, and wherein, in formula (2), $X^1$ and $X^2$ are each independently an oxygen atom or a sulfur atom, $R^3$ and $R^4$ are each independently a monovalent organic group having an aromatic ring or a heterocycle, or $R^3$ and $R^4$ are organic groups that combine with each other to form a ring structure.

8. The monomer composition according to claim 6, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth)acrylate.

9. A curable composition containing the monomer composition according to claim 6.

10. The curable composition according to claim 9, further comprising a polymerization initiator.

11. A composition for a dental material comprising the curable composition according to claim 9.

12. A molded body that is a cured product of the curable composition according to claim 9.

13. The method of manufacturing a monomer composition according to claim 2, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth)acrylate.

14. The method of manufacturing a monomer composition according to claim 3, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth)acrylate.

15. The monomer composition according to claim 7, wherein the iso(thio)cyanate compound (B) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, 4,4'-diphenylmethane diisocyanate, 1,1-(bis(meth)acryloyloxymethyl)ethyl isocyanate and 2-isocyanatoethyl(meth)acrylate.

* * * * *